United States Patent [19]

Malvick et al.

[11] 4,171,158
[45] Oct. 16, 1979

[54] INSPECTION SYSTEM AND METHOD

[75] Inventors: Arnold O. Malvick, Manteca; Wayne W. MacDonald, Oakdale; Carl M. Beckwith, Modesto, all of Calif.

[73] Assignee: TRI/Valley Growers, San Francisco, Calif.

[21] Appl. No.: 793,041

[22] Filed: May 2, 1977

Related U.S. Application Data

[63] Continuation-in-part of Ser. No. 604,596, Aug. 14, 1975, Pat. No. 4,025,422.

[51] Int. Cl.² .......................................... G01N 21/32
[52] U.S. Cl. .................................. 356/239; 250/578; 356/435
[58] Field of Search .............................. 356/237–240, 356/200, 206, 431, 434–435; 250/223, 223 B, 224, 562–563, 571–572, 578, 548, 561; 209/111.7 R, 111.7 T

[56] References Cited

U.S. PATENT DOCUMENTS

| | | |
|---|---|---|
| 3,005,548 | 10/1961 | Flanders et al. ................. 209/111.6 |
| 3,818,223 | 6/1974 | Gibson et al. ........................ 250/223 |
| 3,835,332 | 9/1974 | Bridges ................................. 356/200 |
| 4,025,422 | 5/1977 | Malvick et al. ..................... 250/312 |

FOREIGN PATENT DOCUMENTS 1207489 10/1970 United Kingdom .................... 356/237

*Primary Examiner*—John K. Corbin
*Assistant Examiner*—Wm. H. Punter
*Attorney, Agent, or Firm*—Edward B. Gregg; Alvin E. Hendricson

[57] ABSTRACT

An electronic system for detecting faults or flaws in individual items of a stream of items has a single row of light sensors and a light source and detects the presence of an item between source and detectors, establishes a reference level for comparison that is a function of the individual item under inspection, and produces a fault signal from any individual sensor having a change in incident light that is a predetermined amount greater than the reference level and which occurs within a predetermined adjustable portion of the item passing the sensors.

7 Claims, 7 Drawing Figures

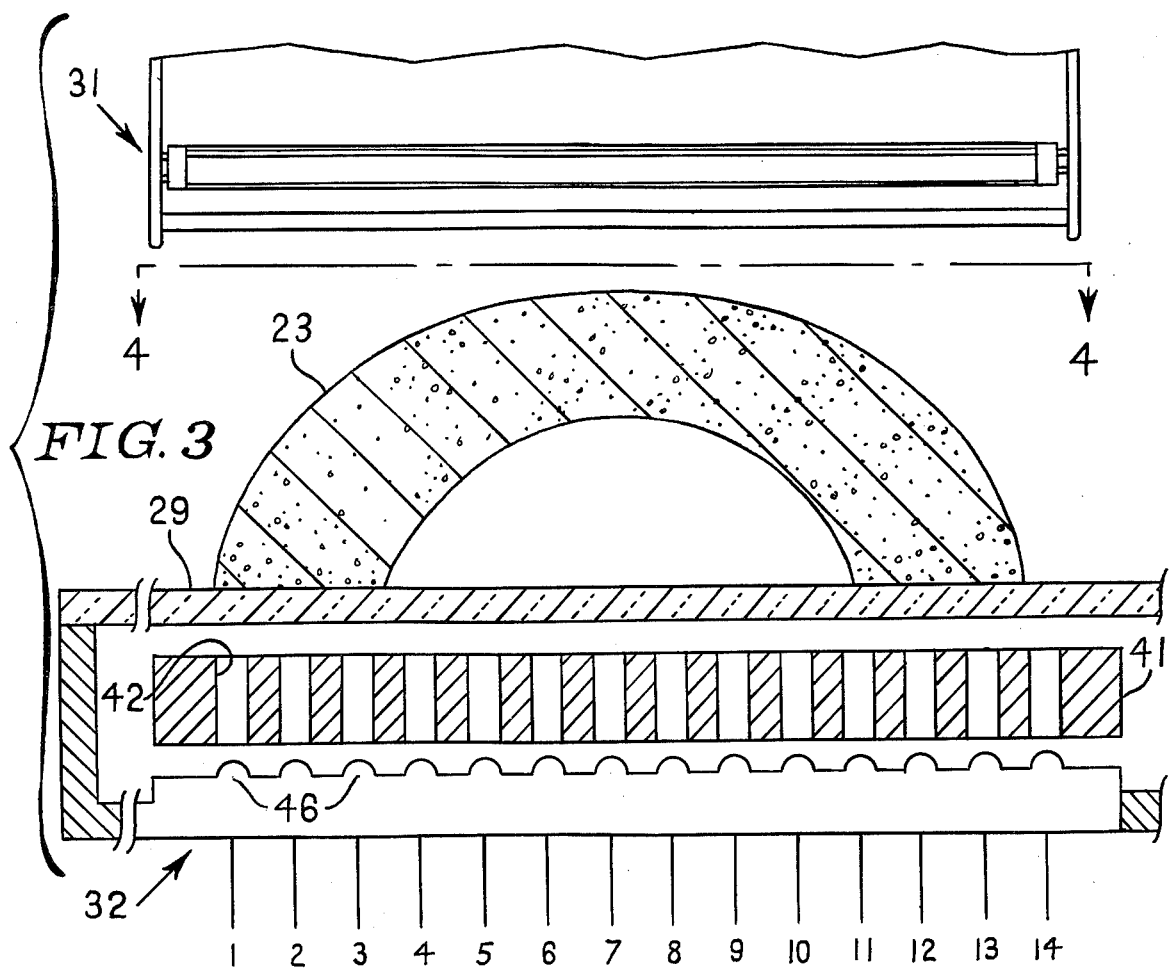
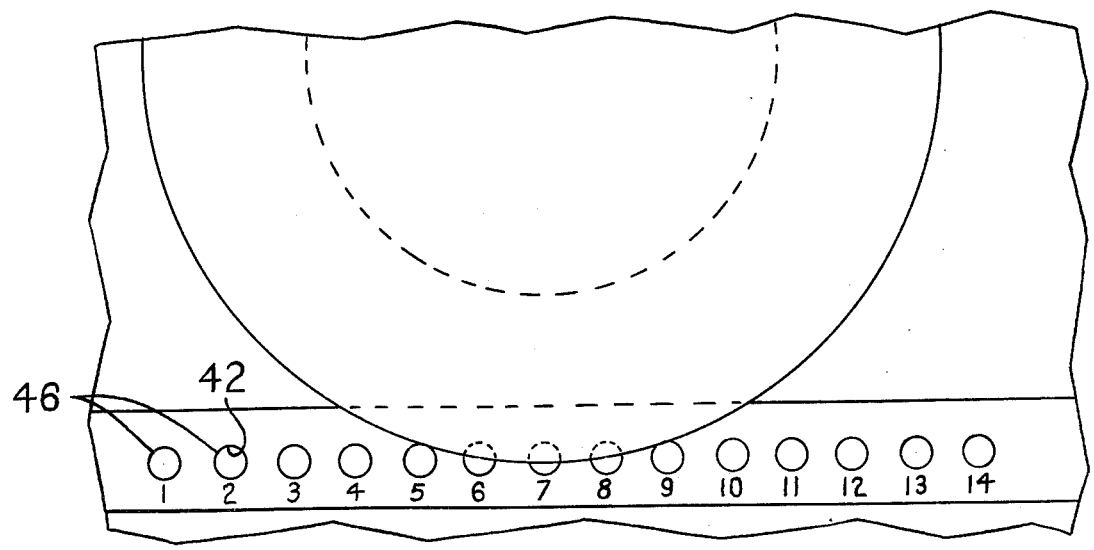

INSPECTION SYSTEM AND METHOD

This is a continuation-in-part of U.S. patent application Ser. No. 604,596 entitled "Method and Apparatus for Inspecting Food Products" and filed in the U.S. Pat. Office on Aug. 14, 1975, now U.S. Pat. No. 4,025,422.

BACKGROUND OF INVENTION

In the inspection of items such as fruits or vegetables, for example, prior to canning, there are normally performed a variety of manual and visual operations aimed at removing any item from the production line that exhibits any one of a variety of flaws. Proceeding with this same example, it is conventional for a substantial number of people to visually inspect each successive item such as an apricot half or peach half prior to canning in order to remove defective items which may, for example, contain a portion of a seed or pit.

There have been developed a variety of different inspection or detection systems for fresh fruit and vegetables or other items of commerce; however, it is still common practice to employ human inspection for many items rather than to employ available automated equipment. One of the reasons for this rejection of available automated equipment is the failure of mechanized or automated equipment to adequately compensate for physical variations in items inspected. As an example of the foregoing, peach halves moving along an inspection line have a relatively wide variation in shape, thickness and exterior opacity. Most mechanized inspection or flaw detection systems fail to accommodate for these variables and thus have not been widely employed.

The present invention provides an inspection or fault detection system which forms a basis of comparison from each individual item passing therethrough and which further provides electronic implementation of a substantial number of control functions required for fault detection, particularly in items having naturally varying characteristics.

SUMMARY OF INVENTION

There is provided by the present invention an improvement in fault or flaw detection of successive items that are passed through the inspection zone of the present invention. Individual items to be inspected hereby may have varying properties and physical configurations and yet it is necessary to detect particular faults in each of such items. In order to "automate" inspection, it is necessary to properly identify the "presence" of an item to be inspected and to establish a standard against which inspection is compared in order to identify items having a fault or flaw of unacceptable proportions. The present invention establishes this standard in terms of each individual item being inspected.

The mechanized or automated inspection of the present invention also generates many internal problems which must, and are, first overcome before it is possible to trust the results of this inspection. Only by building in to the present invention a plurality of "checks and balances" or safeguards, is it possible for the system and method hereof to be truly feasible in commerce. The present invention is in fact fully operable to produce the results claimed therefor and this has, in fact, been established in one of the largest packing houses in the world.

DESCRIPTION OF FIGURES

The present invention is illustrated as to a single preferred embodiment in the accompanying drawings, wherein:

FIG. 3 is a transverse sectional view of a portion of the inspection station of FIG. 1 taken in the vertical plane 3—3 thereof;

FIG. 4 is a partial sectional view of the inspection station taken in the horizontal plane 4—4 of FIG. 3;

DESCRIPTION OF PREFERRED EMBODIMENT

The present invention provides a fully automated system and method for inspecting items for flaws or faults. The invention may be employed for the inspection of a wide variety of different items; however, the inspection of fruit or vegetables poses particular problems, in part because of the somewhat irregular configurations thereof and the inevitable variations between successive items. In the following description a preferred embodiment of the present invention is referenced to the detection of peach pit fragments in successive peach halves that are to be canned. It will be appreciated that in this example it is necessary to detect very small fragments in or on a very irregular surface within peach halves having varying sizes and shapes and, furthermore, that the detection of every fragment is very important. Peach pit fragments are very hard and are often sharp so that the inclusion of even one small fragment in an entire can of peaches cannot be tolerated. Furthermore, the nature of peach pit cavities renders visual identification of a small pit fragment very difficult so that a person eating canned peaches relies heavily upon the prior inspection during processing.

Figure 1:
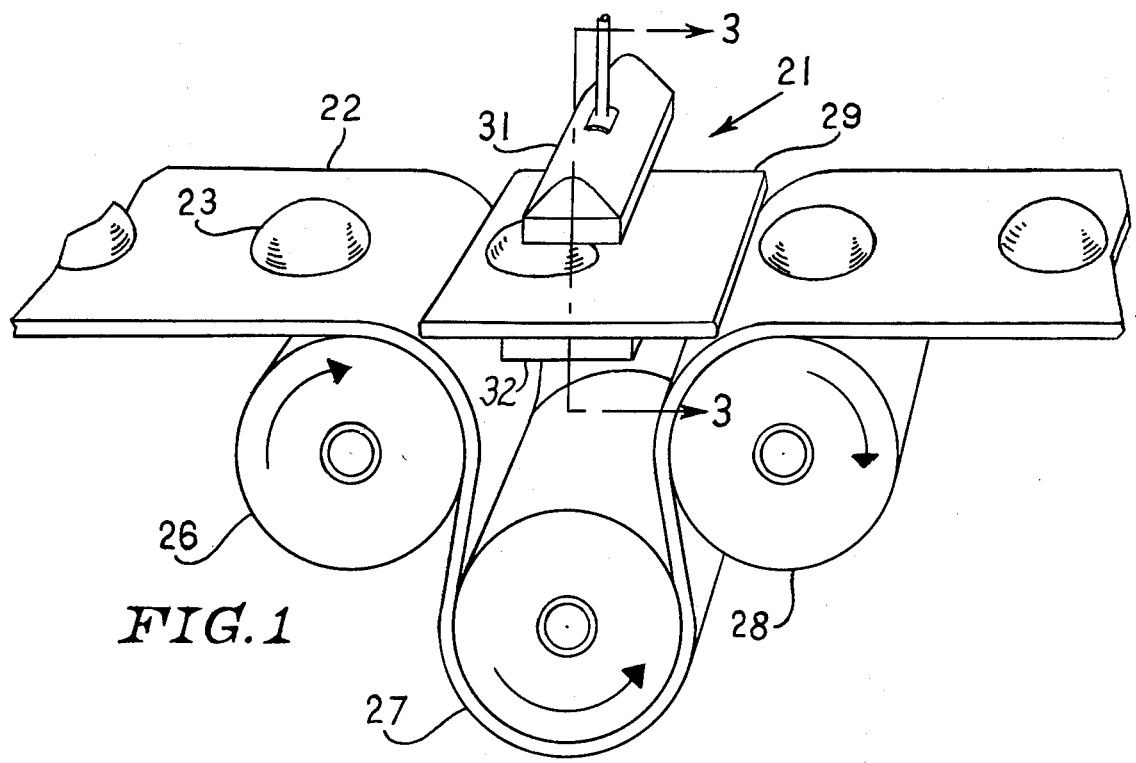
FIG. 1 is a partial perspective view of an inspection station in accordance with a preferred embodiment of the present invention.

Referring now to the drawings, there will be seen to be shown in FIG. 1 a schematic perspective illustration of an inspection station 21 in accordance with the present invention. A conveyor belt 22 carries peach halves 23, cup down, to and from the station and, as illustrated, the conveyor belt 22 may pass over a roller 26, under a roller 27 and back up over a roller 28 so as to form a loop with an open top, as shown. A transparent plate 29 is disposed across this open top of the loop on the conveyor belt so that peach halves 23 rapidly moved by the conveyor belt 22 will slide on to the plate 29 and thereacross back on to the conveyor belt. The successive peach halves are disposed in cup-down relationship to the conveyor belt and are disposed in single file as by a conventional shaker and the peach halves are aligned in the center of the belt as by appropriate tunnel or directing means.

The inspection station 21 includes an overhead source of radiation 31 which may, for example, comprise tungsten filament lamps directing light downwardly on to the transparent plate 29. Immediately beneath the transparent plate 29 there is disposed a sensor array 32 including a single row of phototransistors or other optical sensors disposed transversely of the direction of belt travel together with associated electronic circuitry for the generation and processing of control and detection signals. The row of sensors in the array 32 thereof is sufficiently long to ensure viewing of the entire pit cavity of each peach half passing over the transparent plate 29, with these peach halves being properly centered on the belt prior to passing over the row of sensors. It is noted that the response characteristics of conventional phototransistors are more sensitive to infrared or wavelengths close thereto than to other wavelengths in the visible spectrum and thus the source of radiation preferably has a high intensity of radiation in this range of wavelengths; however, alternative photosensors and light sources may be employed.

Figure 2:
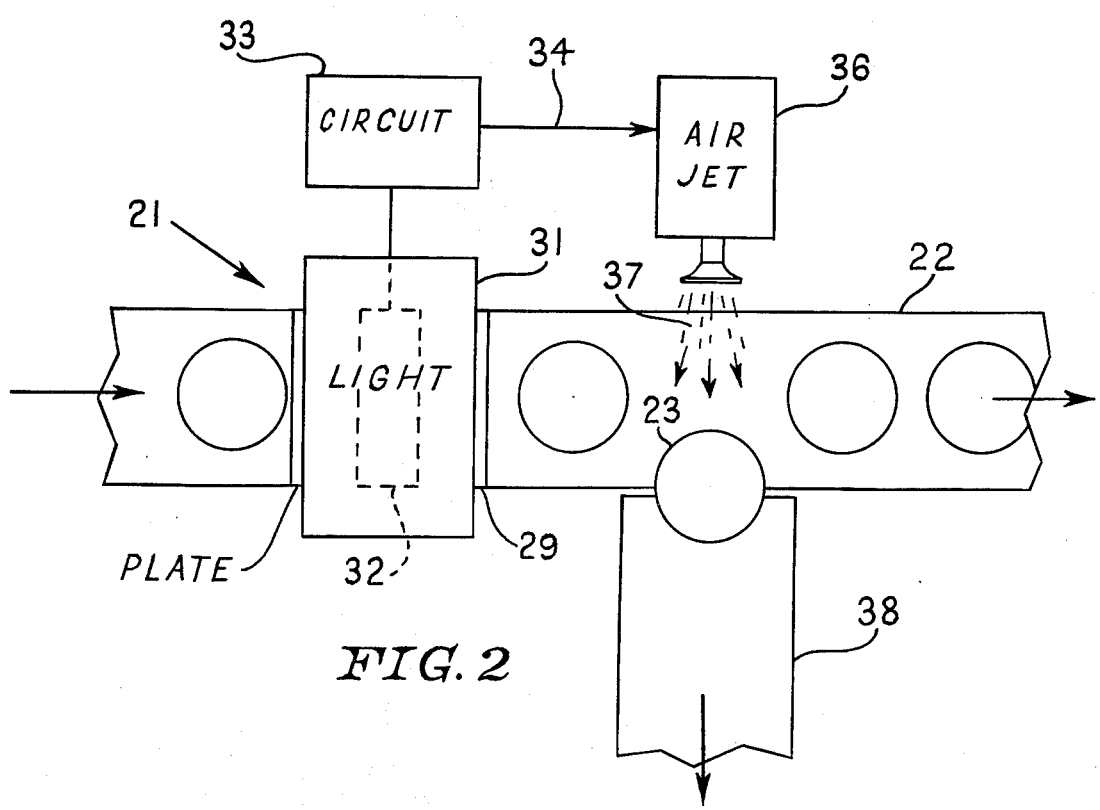
FIG. 2 is a schematic plan view of inspection and segregation equipment in accordance with the present invention.

The purpose of the inspection station 21 of FIG. 1 is to identify the presence of large or small pit fragments in successive peach halves passing therethrough. This information is then employed for the purpose of segregating faulty peach halves from the remainder. Referring to FIG. 2 there will be seen to be schematically illustrated means for removing peach halves having detected pit fragments therein. The sensor array 32 is connected to appropriate circuitry 33 which produces an output signal on a line 34 for operating some type of segregating equipment such as, for example, an air jet 36 disposed adjacent the conveyor belt 22 on the outlet side of the inspection station for controllably expelling a brief jet of air 37 directed laterally across the top of the conveyor belt so as to force a selected peach half 23 off the conveyor belt and possibly on to another conveyor belt 38 disposed below and moving laterally of the conveyor belt 22. It will be appreciated that there are a variety of different conventional means and systems for separating items such as peach halves and the air jet system illustrated is only exemplary of one type thereof. The present invention is capable of operating with a wide variety of different segregating means including the one illustrated.

Reference is now made to FIGS. 3 and 4 of the drawings illustrating some details of the inspection station. It will be seen that the radiation source 31 is disposed a sufficient distance above the transparent plate 29 to readily accommodate the passage of successive peach halves 23 along the transparent plate between adjacent portions of the conveyor belt loop. Immediately beneath the transparent plate 29 there is disposed a block 41 having a plurality of small parallel vertical passages 42 disposed therethrough in alignment across the plate and the sensor array 31 is disposed immediately beneath this block. The sensor array 31 includes a plurality of photosensors such as phototransistors 46 suitably mounted in a line transversely across the transparent plate 29 and disposed with one sensor beneath each vertical passage 42 in the block 41. In this manner each sensor views a small area on the underside of a peach half passing over the transparent plate. It is important that the individual sensors have shields or the like above them in order to control the beam angle from which sensors will receive light. This ensures that each sensor will "look at" a sufficiently small area of a peach half to detect small pit fragments and the sensors and light guides are mounted as close as possible to the transparent plate beneath same.

It will be appreciated that the amount of light reaching each sensor from the radiation source 31 passing through a peach half is dependent upon the size or thickness of the peach, the presence of skin on the peach, the scattering of light internally of the peach, the presence of a pit or pit fragment in the peach, and the optical density of the peach, which is determined by the naturally-occurring characteristics of the peach allowing more or less light to be transmitted therethrough. Variations of light falling upon individual sensors are herein employed in such a manner as to minimize pit fragment identification that might be caused by any of the above-noted conditions except pit fragment presence.

In the embodiment of the present invention illustrated herein there are provided a substantial number, such as fourteen, phototransistors or sensors identified by these numbers in FIGS. 3 and 4. The present invention operates to provide an output from each of these fourteen sensors independently; however, the invention hereof further provides for the processing of signals from more than one of these sensors for each determination or identification of a pit fragment in a peach half passing over the line of sensors. It is in fact provided by the present invention that certain combinations of sensor outputs shall be employed to establish particular conditions which are then employed in relationship to individual sensor signals to produce a pit fragment indication or detection signal.

Figure 5:
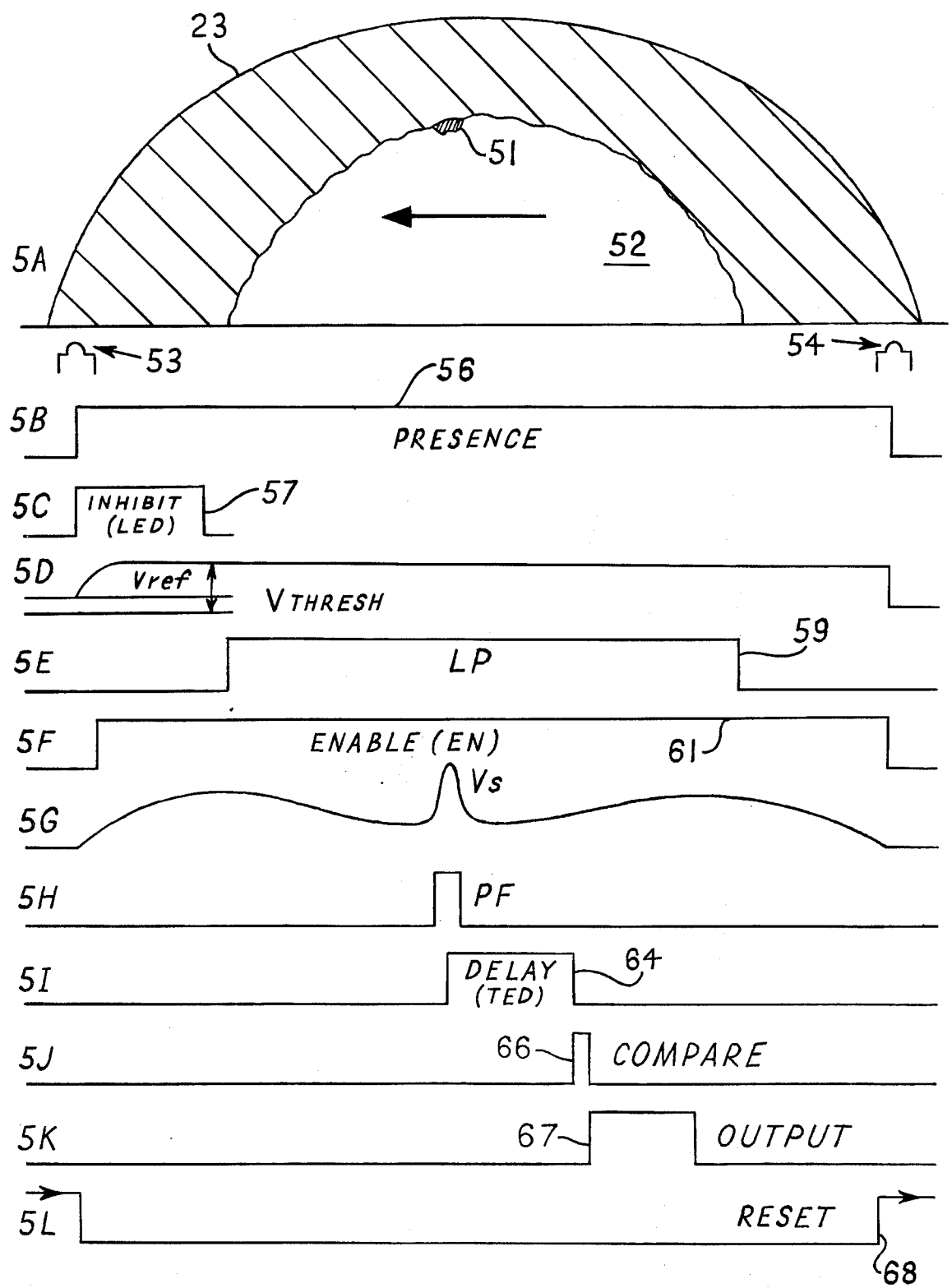
FIGS. 5A–L are charts of signal waveforms as generated in the present invention and spatially related to an item such as a peach half under inspection.

The present invention and the general operation or process hereof may be best understood by referring to FIG. 5 wherein there is illustrated at 5A a peach half 23 moving to the left in the drawing and having a peach pit fragment 51 in the peach pit cavity 52 thereof. In order to visualize the process of the present invention and the operation of the apparatus hereof, FIG. 5 illustrates signals that may be generated by the relative movement of a peach half and the sensor array; however, in this figure it might be best considered that the sensor array moves to the right across the figure from an initial position, as indicated at 53, to a final position, as indicated at 54. In FIG. 5 there are illustrated at 5B through 5L various signals that may be generated by the passage of a peach half over the sensor array 31.

The first thing that the present invention does as a peach half passes over the sensor array is to generate a PRESENCE signal, as indicated at 5B. This PRESENCE signal 56 is generated by comparing the highest output signal from one of some predetermined number of sensors with a previously determined voltage level. In accordance with the present invention a high voltage level from a sensor or at least from the amplifier connected thereto indicates a "dark" condition so that, with no peach in the sensor area, the output from the sensor provides a relatively low voltage. In accordance herewith sensors 4, 6, 9 and 11, for example, are employed as reference sensors and the PRESENCE signal may be generated by comparing the outputs of sensors 4, 6, 9 and 11, for example, to an adjustable voltage level. As soon as any one of these four sensors produces an output signal having an amplitude greater than some predetermined adjustable voltage level, there is generated a PRESENCE signal, as indicated at 56. This signal only indicates to the present invention that a peach half is in fact in the process of passing over the sensor array and does not in any way indicate the presence or absence of a pit fragment. As soon as the PRESENCE signal 56 is generated, there is established a delay or inhibit condition, herein termed a Leading Edge Delay or L.E.D., which prevents any indication of a pit fragment and this condition may be established by a leading edge timer, as described below. The inhibit condition is indicated by the pulse 57 at FIG. 5C and is predetermined to have a duration equal to slightly less than the time between the passage of the leading edge of a peach half over the sensor array and the passage of the leading edge of the pit cavity over the sensor array. It will be appreciated that this time is a function of the speed of the conveyor belt which estblishes the velocity of the peach half over the sensor array. As indicated at FIG. 5C, the inhibitor pulse, as it is therein identified, terminates slightly before the pit cavity reaches the sensor array. This inhibition or time delay is provided for the purpose of preventing any possible false pit fragment indication because of a substantial thickness of peach half disposed above the sensor array prior to passage of the peach cavity over the array. This inhibit condition is required because the output of one or more sensors may rise more rapidly than the others at the leading edge of a peach half. Depending upon which sensor or sensors are effected, the requirements for signal processing as described below may be upset. Thus, for example, one sensor output might go very high before all of the sensors employed in establishing an average were even covered by a peach half.

The present invention furthermore provides for the establishment of a comparison level in order to determine whether or not the signal from any individual sensor of the array 31 is in fact indicative of a pit fragment in the peach half passing over the array. The foregoing is accomplished by the establishment of a reference level signal by averaging the signals from sensors 4, 6, 9 and 11, for example, and adding to this average a threshold signal or voltage to produce $V_{REF}$ as a basis for comparing subsequent sensor signals. It will be appreciated that the physical characteristics of successive peach halves passing over the sensor array will vary and thus the present invention takes into account these variations by comparing individual sensor signals to a signal or reference derived from the individual peach half being inspected. It will be noted that an average of the signals from some predetermined number of sensors, such as sensors 4, 6, 9 and 11, will dip or reduce as the peach cavity passes over the sensor array because a thinner peach section is disposed directly above the sensors at this time. In accordance with the present invention the reference level or $V_{REF}$ is sustained during passage of the individual peach half over the sensor array by applying the $V_{REF}$ to a capacitor for charging the capacitor at a rapid rate and then allowing only slow capacitor discharge. This is indicated at FIG. 5D wherein $V_{REF}$ is shown to include $V_{THRESH}$ and to be maintained at a fairly substantial level over the entire time of peach half passage over the sensor array. It will be noted that the addition of this added threshold voltage $V_{THRESH}$ to the average voltage of sensor signals from sensors 4, 6, 9 and 11 is necessary because at least some of the sensors will obviously have a higher output than the average even though no pit fragment is in fact present.

The addition of the threshold voltage to the average voltage signal from the four selected sensors provides a band above which any individual sensor or channel thereof must rise before determination is made that a pit fragment is in fact present in the peach half passing over the sensor array. The narrower this band the smaller the size of the pit fragment that can be detected; however, the narrower this band, the more susceptible the system is to false pit indications due to the variations in peaches as identified above. Thus the threshold voltage $V_{THRESH}$ is adjustable so that, while operating the present invention or carrying out the method hereof, it is possible to set the sensitivity.

It will be appreciated that a peach half passing over the sensor array may contain a half pit, a whole pit or a very large portion of a pit half. Under these circumstances so much light is blocked from the sensors that the average level of the four channels or sensors 4, 6, 9 and 11 may be at a saturation level or close enough thereto that when the threshold voltage is added to this average, no individual channel could exceed it. Under these circumstances, it is obvious that a peach pit or a substantial portion of a pit (not shown) is present and, consequently, the present invention operates to produce a large pit or LP pulse 59, as indicated at FIG. 5E. This is accomplished by comparing $V_{REF}$ with a predetermined adjustable voltage level and, when $V_{REF}$ exceeds this level, there is produced an LP signal indicating the presence of a large pit fragment without regard to other processing of the present invention. At this point it is noted that the waveforms or pulses indicated in FIG. 5 are not intended to depict actual waveforms nor relative amplitudes, unless otherwise indicated, but instead are intended primarily to indicate time relationships of the various conditions established by the detection system and method hereof. Thus it will be seen that LP can only be generated during passage of the peach cavity 52 over the sensor array, as indicated in FIG. 5E by the alignment of the LP pulse 59 with the peach cavity 52 of FIG. 5A.

Considering further the identification or detection of a small pit fragment, the present invention provides for the establishment of an ENABLE condition which is accomplished by comparing $V_{REF}$ to a different predetermined adjustable voltage than that employed to generate the PRESENCE signal and generating ENABLE when $V_{REF}$ exceeds this level. The foregoing partially compensates for areas of a peach where one sensor may be at a higher level with respect to $V_{REF}$ and yet the pit cavity is not yet over the sensor area. In FIG. 5F there is indicated an ENABLE pulse 61.

The output signal or voltage level from each of the sensors 1 to 14 is continuously compared to $V_{REF}$ during the ENABLE condition or the duration of the ENABLE pulse 61, as indicated in FIG. 5F. The comparison can produce no result during the inhibit period 57 but subsequent thereto, as indicated at FIG. 5G, a sensor signal $V_S$ which has an amplitude in excess of $V_{REF}$ will in fact produce a pit fragment or PF pulse or signal, as indicated at FIG. 5H. It will be seen that $V_S$ in FIG. 5C is aligned with the pit fragment 51 of FIG. 5A and that the PF signal is then concurrently generated inasmuch as the ENABLE signal 61 is in effect.

In order to prevent false indications at the trailing edge of the peach, the present invention provides a trailing edge detector (TED), as described below, which is actuated by a concurrence of PF and ENABLE to provide a delay, as indicated at 64 of FIG. 5I. The time duration of this delay 64 may be substantially the same as the time duration of inhibit 57. At the termination of this delay period the present invention produces a very short COMPARE pulse 66 and a determination is made as to the coincidence in time between the COMPARE pulse 66 and the PRESENCE pulse 56.

Upon the determination that the PRESENCE pulse is still persisting during the COMPARE pulse, there is then produced an output pulse 67, as indicated at FIG. 5K. This output pulse 67 would occur earlier if a large pit fragment had been detected to produce an LP signal 59, inasmuch as an output pulse is separately generated immediately upon generating an LP signal.

In brief summary of the foregoing, it is noted that the trailing edge timer or delay 64 is only initiated by a coincidence of PF and ENABLE, i.e., the detection of a pit fragment during the time that $V_{REF}$ is greater than a predetermined adjustable voltage level. The COMPARE pulse 66 is then employed to check with the PRESENCE pulse 56 to ensure that a peach cavity and not the trailing edge of the peach was in fact physically located above the sensor array during the detection producing an output pulse 67. The output pulse may be employed, as indicated in FIG. 2 of the drawings, to operate segregating equipment such as the air jet 36. In some installations the segregating means may be located sufficiently close to the sensors that the air jet, for example, need only be operated for a limited time sufficient to remove the peach half with a detected pit fragment. Other installations may require a time delay, as in the generation of the output signal for example, in order to operate the segregating means at the time the "detected" peach half has been moved by the belt into position for segregation. Such time delay may be included in a deflection timer described below in connection with FIG. 7, by inclusion of a further like timer or appropriate shift register means if the spacing of sensing and deflecting stations is greater than the spacing of peach halves so that a number of peach halves can be kept track of simultaneously while traveling between stations. Thus the deflect timer may include delay means incorporating a time delay determined from the belt speed and physical separation of sensing or inspection station and segregating station.

As the peach half passes beyond the sensor station or line of sensors, the present invention operates to reset the circuitry. As the output level of the particular sensors employed to produce PRESENCE signal falls below the COMPARE level, there is produced a PRESENCE or RESET signal, as indicated at 68 of FIG. 5L. This RESET signal is employed to discharge the capacitor storing $V_{REF}$ as by means of a transistor and the capacitor is rapidly discharged thereby. The RESET signal remains at a ligh level until the presence of another peach half is detected and the evaluation sequence is again initiated. It is noted that the RESET signal is employed to maintain the capacitor storing $V_{REF}$ discharged until after the PRESENCE signal 56 is generated or goes to a high level in order to ensure that the leading edge timer will be triggered to generate an inhibit pulse 57 before PF and EN can both go to a high level.

Figure 6:
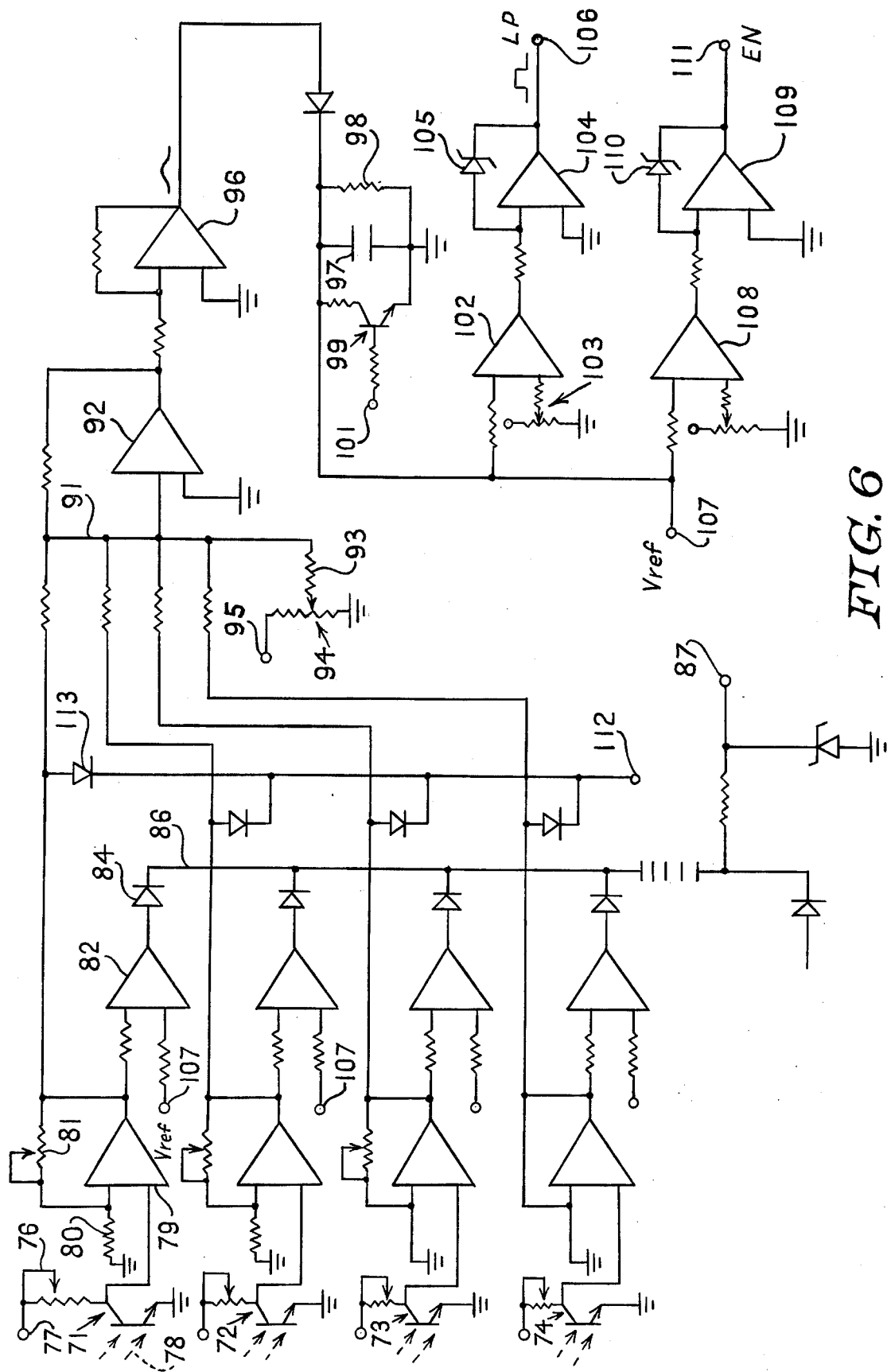
FIG. 6 is a circuit diagram of circuitry for producing electronic signals employed in the present invention.

Reference is now made to FIG. 6 of the drawings illustrating a circuit for generating the particular electronic signals identified above and illustrated in FIG. 5. It is noted that the circuitry of FIG. 6 may be termed a "size compensation circuit" inasmuch as the signals generated therein are, in fact, primarily directed to controlling or limiting pit detection to the pit cavity of a peach half bearing in mind that the size of the cavity may vary from one peach half to another. At the left of FIG. 6 there are illustrated four of the sensors of the array 32 and these are shown to comprise photosensitive transistors 71, 72, 73 and 74. Taking the example wherein the 4th, 6th, 9th and 11th sensors are employed for reference purposes, the transistors 71 to 74 are considered to comprise these sensors of the overall array. Each of the sensors is connected to a separate channel and the channels of the four reference sensors 71 to 74 are identical. Considering then the channel of sensor 71, it will be seen that the photoresponsive transistor 71 has the emitter grounded and the collector connected through a sensitivity control in the form of a variable resistor 76 to a positive power supply terminal 77. Radiation incident upon the sensor 71, as indicated by the dashed arrows 78, will cause conduction of the transistor and the collector thereof is shown to be connected to one input terminal of the sensor amplifier 79 having the other input terminal connected to ground through a resistor 80. A variable feedback resistor 81 is provided for controlling the amplification of the sensor amplifier 79. It will be noted that the gain of the amplifier 79 is actually determined by the ratio of the resistors 80 and 81 with the gain being equal to one plus the ratio of the value of resistor 81 to the value of resistor 80. The variable resistor 76 in the collector circuit of the transistor 71 controls the current and hence the voltage input to the amplifier. With the amplifier gain also being adjustable, it will be seen that the channel can be calibrated at two specific levels. This capability makes the channel output voltage versus incident radiation very nearly equal for all the channels over a desired range.

The output of sensor amplifier 79 is resistively coupled to one input of a comparator 82 and the other input of this comparator is resistively coupled to a terminal having a voltage $V_{REF}$ applied thereto. $V_{REF}$ is generated by additional portions of the circuit of FIG. 6, as described below. The output of the comparator 82 is coupled through a diode 84 to a common line 86 which is, in turn, connected to the output of each of the 14 channels. It will be noted that each of the sensors is connected in the same manner as sensor 71 described above with the output of each of the sensor channels being coupled to the common line 86. It will be appreciated that, when any sensor produces a signal through the amplifier thereof which is greater in amplitude than $V_{REF}$, there will be applied a signal to the common line 86 and this line is shown to be resistively coupled to a terminal 87 which is shown to be grounded through a Zener diode and at which there then occurs a pit fragment or PF signal. Any one sensor is thus capable of producing a PF signal at terminal 87 and, with the very close spacing of sensors across the sensing station, it will be seen that a very minute pit fragment will be detected by the present invention.

The outputs of the channels connected to sensors 71 to 74 are each connected through like resistors to a line 91 which, in turn, is connected to one input of an amplifier 92 and through a fixed resistor 93 to a potentiometer 94 tied between *ground* and to a *positive* power supply terminal 95 so as to comprise a threshold adjustment. In this manner $V_{REF}$ is generated by averaging the output of the channels of the four sensors 71 to 74 and adding thereto a threshold voltage established by the threshold adjustment. The output of the amplifier 92 is resistively coupled to the input of an inverter amplifier with unity gain 96 to thus produce $V_{REF}$ having a waveform somewhat as illustrated at the output of the amplifier 96. This signal is coupled through a diode to one side of a capacitor 97 having the other side grounded. A resistor 98 is connected across the capacitor 97 and also a transistor 99 is resistively coupled across the capacitor 97. The base of the transistor 99 is connected to a terminal 101 adapted to receive a RESET signal for the purpose of discharging the capacitor 97 after a sensing operation has been completed. The capacitor 97 will be seen to be charged to a voltage which is one diode drop below $V_{REF}$ and, by the use of a very large resistor 98 in parallel therewith, the charge in this capacitor is maintained substantially constant over the time period of each sensing operation.

$V_{REF}$ is also resistively coupled to one input of an amplifier or comparator 102 having the other input connected to the movable element of a potentiometer 103 connected between ground and a positive power supply terminal. The output of the amplifier 102 is connected through a further amplifier 104, as illustrated, to an output terminal 106 for applying a signal thereto upon the occurrence of a large pit in the peach half being evaluted or inspected and this signal is herein denominated as LP. The potentiometer 103 establishes an adjustable voltage level against which $V_{REF}$ is compared in the amplifier 102 so as to produce an LP signal when $V_{REF}$ exceeds this voltage level. A Zener diode 105 is connected across the amplifier 104, as shown, to limit or clamp the output to proper levels for following logic circuitry.

$V_{REF}$, as stored upon the capacitor 97, is applied to an output terminal 107 that will be seen to be connected to one input of each of the comparators 82 in the sensor channels. In addition, $V_{REF}$ is employed to generate an ENABLE or EN signal by resistively coupling $V_{REF}$ to one input of an amplifier or comparator 108 having the other input resistively coupled to a threshold adjustment in the same manner as described above for comparator or amplifier 102. The output of comparator 108 is resistively coupled through another amplifier 109, as illustrated, to a terminal 111 at which the ENABLE or EN signal appears when $V_{REF}$ exceeds the adjusted threshold voltage. A Zener diode 110 is connected in parallel with the amplifier 109 for the same purpose as diode 105.

The circuit of FIG. 6 also generates a PRESENCE signal by coupling the output of the amplifiers 79 of the sensor channels 71 to 74 through diodes 113 to the terminal 112.

The circuit of FIG. 6 produces sensor signals which are compared with a reference voltage $V_{REF}$ generated in the circuit from signals produced by each peach half passing through the sensing station. A pit fragment signal PF is produced whenever the output from any one sensor exceeds this adjustable reference voltage. Additionally, FIG. 6 generates an LP signal, a signal employed to produce the PRESENCE signal and an ENABLE signal. All of these signals are employed in accordance with the present invention in a timing and logic circuit, as illustrated in FIG. 7.

Figure 7:
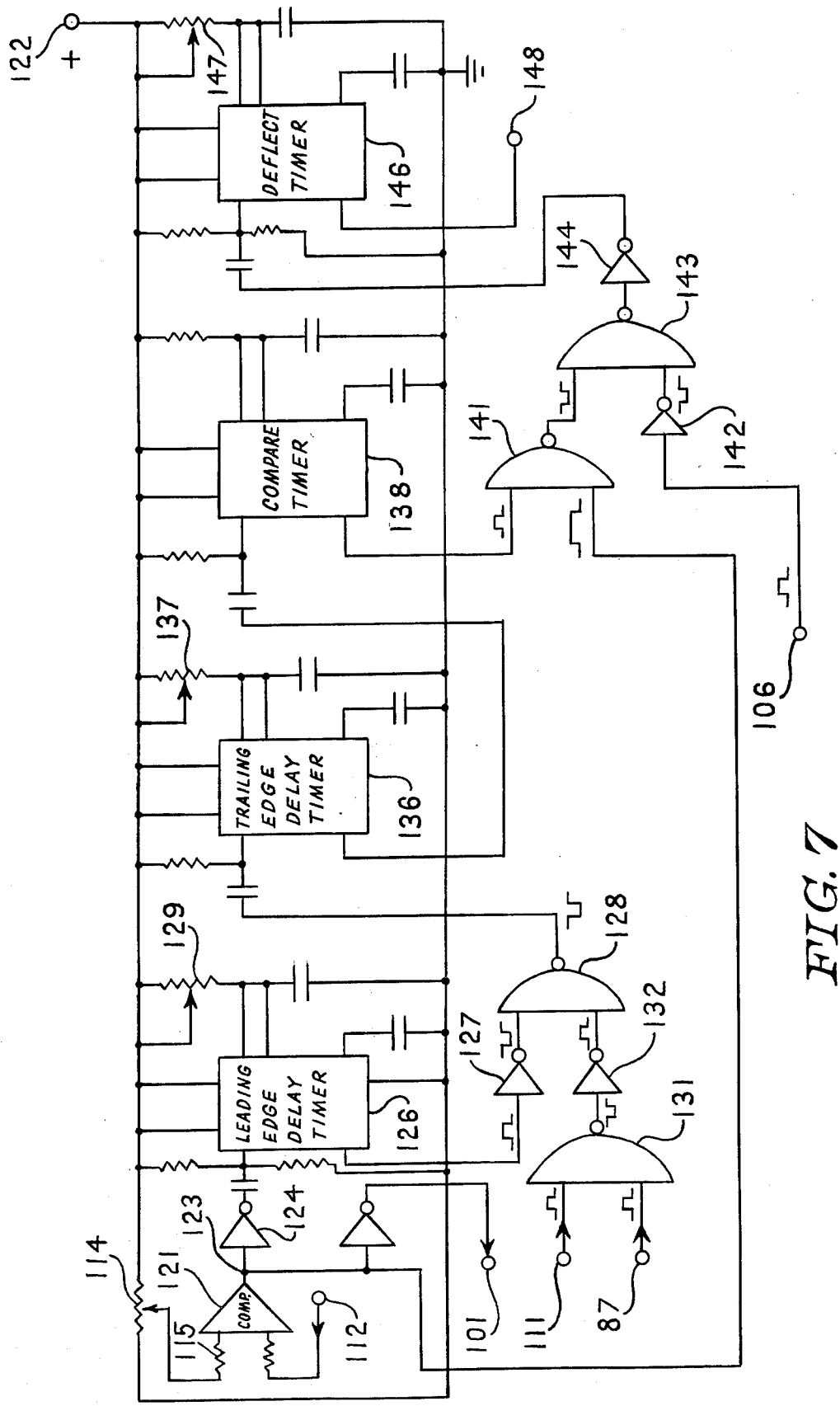
FIG. 7 is a diagram of logic circuitry operating upon the signals generated in the circuit of FIG. 6.

Considering now the circuit of FIG. 7, it is first noted that output terminals of FIG. 6 are labeled with the same numeral in FIG. 7 as in FIG. 6. The signal at terminal 112 of FIG. 6 is applied to a comparator 121 having the other input thereof resistively coupled through a resistor 115 to a voltage divider or potentiometer 114 connected between a positive power supply terminal 122 and ground. When the amplitude of the signals from any one of the sensors 71 to 74 exceeds a predetermined level as established by the comparator 121, there will then be produced an output from the comparator at a terminal 123 which in fact comprises the PRESENCE signal 56 of FIG. 5B. It is noted that the convention employed in the present invention provides a high voltage level output from a sensor when light is blocked to the sensor and thus, with no peach in the sensor area, the output from the sensors is a relatively low voltage. It will thus be seen that a PRESENCE signal is positive or high voltage and in the circuit of FIG. 7 this signal is inverted in an inverter 124 and capacitively coupled to an input of a leading edge delay timer 126. The timer 126 is conventionally connected as illustrated to produce a positive output signal that is applied through an inverter 127 to one input of a NAND circuit 128. The output of the timer 126 has an adjustable duration as set by a variable resistor 129 and this output is termed the inhibit pulse, as illustrated at 57 of FIG. 5C.

The pit fragment signal PF at terminal 87 and the ENABLE signal EN at terminal 111 are applied as inputs to a NAND circuit 131 for producing an output upon concurrence of these signals and this output is inverted in an inverter 132 and applied to the other input of the NAND circuit 128. As long as the inhibit pulse 57 from the leading edge delay timer 126 exists, no output will be produced from the NAND circuit 128; however, an output will be produced upon expiration of the inhibit pulse if PF and EN is high or later goes to a high value and this output is capacitively coupled to an input of a trailing edge delay timer 136 in order to determine whether or not PF and EN first went high at or near the trailing edge of the peach half. The timer 136 produces a delay pulse 64, as shown at FIG. 5I, and the duration thereof is adjustable by means of a variable resistor 137 in conventional manner. This delay pulse from the timer 136 is employed to generate a compare pulse by coupling the delay pulse to an input of a compare timer 138. The compare pulse is a very short pulse generated at the end of the trailing edge timer pulse and this compare pulse is applied as one input of a NAND circuit 141 having the other input thereof connected to terminal 123 for application of the PRESENCE pulse thereto. Thus the circuit operates to produce an output signal from the NAND circuit 141 if the compare pulse is generated during the existence of the PRESENCE pulse, i.e., during the time that a peach half is over the line of sensors.

As noted above, the circuit of FIG. 6 generates a large pit signal LP at terminal 106 thereof when $V_{REF}$ exceeds a predetermined high level. In FIG. 7 this LP signal at terminal 106 is shown to be inverted by an inverter 142 and applied as one input to a NAND circuit 143 having the other input applied from the output of NAND circuit 141. The circuit 143 operates to pass a signal or produce an output upon the receipt of either the inverted LP signal or the output of NAND circuit 141 denoting coexistence of the compare and PRESENCE signals.

In the circuit of FIG. 7 the output of the NAND circuit 143 is inverted in an inverter 144 and applied as an input to a deflect timer 146 having a duration which is controllable by a variable resistor 147 for producing an output at a terminal 148 that is employed to operate peach half deflection means such as illustrated in FIG. 2. It will be appreciated that the timer 146 operates to produce an output signal at such time that a peach half having a detected pit fragment has moved from the sensing station to the deflecting location. If the deflecting location can be located close enough to the sensing station, no electronically generated time delay is necessary. The time required for solenoid valves or other physical devices to actuate can take as long as it takes the peach half to reach the deflecting station. Also, the duration of the deflect timer output pulse may be adjusted to be long enough to compensate for variations in peach size and location over sensors when pit is detected.

There has been described above a preferred embodiment of the present invention particularly directed to detecting pit fragments of any size from a full pit to a very minute fragment in successive peach halves passed over a sensing station. The problems associated with identifying a flaw such as a pit fragment in items of varying size and shape such as successive peach halves are herein overcome by the provision of size compensation means or circuitry. Such means prevent the generation of false signals as might occur. It is noted in this respect that the length of the inhibit pulse 57 produced by the leading edge delay timer must be less than the time between the passage of the leading edge of a peach half and the passage of the forward edge of a pit cavity over the line of sensors. It will be noted that this time is a function of the belt speed. As discussed above, this inhibiting of the present invention precludes the generation of a false signal prior to passage of the peach half cavity over the line of sensors. The trailing edge timer is provided for the purpose of preventing the possible generation of a false signal as the trailing edge of the peach half passes over the line of sensors. It is further noted with respect to FIG. 7 that the PRESENCE signal at terminal 123 is inverted and applied to the reset terminal 101 so that a negative signal is applied to this reset terminal while the PRESENCE signal is in existence. As soon as the PRESENCE signal terminates, indicating the passage of the trailing edge of the peach half over the line of sensors, the voltage at reset terminal 101 rises and, inasmuch as this terminal is coupled to the base of the transistor 99 in FIG. 6, it will be seen that the transistor then conducts to rapidly discharge the capacitor 97 storing $V_{REF}$. This capacitor 97 is very rapidly discharged immediately upon termination of the PRESENCE signal and this capacitor is maintained in a discharged state until the PRESENCE signal again goes to a high value. The PRESENCE signal is a pulse, as indicated at 56 in FIG. 5B, and thus it will go to a high value substantially immediately so as to actuate the leading edge delay timer before the capacitor 97 can recharge to $V_{REF}$. This then ensures triggering of the leading edge timer 126 before PF and EN can both go high so that the trailing edge timer cannot be actuated before the leading edge timer.

In the detection of a pit fragment with the present invention it will be seen that the blocking of light to any one sensor of the array thereof is sufficient to indicate the presence of a pit fragment; however, the present invention provides for the processing of signals from a number of sensors in order to determine whether or not a peach half does contain a pit or pit fragment. In the present example of the present invention as described above, four sensors are employed for the processing of signals therefrom to identify the presence of a peach half and to identify the location of the cavity therein; however, it will be appreciated that a different number of sensors could be employed for this purpose and also that different individual sensors may be utilized in this respect.

The present invention is capable of various modifications, particularly with regard to simplification thereof. It is possible, for example, to employ the present invention to detect only large pits and this might be accomplished by applying a simple reference voltage generated by a potentiometer connected between ground and a positive supply terminal as an input to comparators 82 in place of $V_{REF}$ and then employing the signal at terminal 87 of FIG. 6 as an input to the deflect timer 146 of FIG. 7. Normally fewer sensors, such as six or eight sensors, are adequate to scan a pit cavity area for large pit fragments. It is also possible for detecting large pit fragments to connect the outputs of a number of sensor amplifiers 79, as in FIG. 6, through separate diodes to one input of a single comparator 82. The other input of this comparator may be provided from a potentiometer connected between ground and a positive power supply terminal with the comparator output being converted to proper signal levels to drive output circuitry as at the deflect timer 146 of FIG. 7. The foregoing are merely samples of various circuit options possible with the present invention and others are also possible.

The present invention has been described above with respect to a signal preferred embodiment thereof; however, it will be appreciated that many modifications and variations may be made within the scope of the present invention. Clearly circuit modifications and variations are possible, for example, and thus it is not intended to limit the present invention to the precise terms of description nor details of illustration.

What is claimed is:

1. An inspection system for identifying the presence of flaws in successive items conveyed past an inspection station having a light source directed upon a plurality of closely spaced light sensors disposed in a line across the direction of movement of said items and on the opposite side thereof from said light source comprising means averaging the output signals of selected sensors and adding thereto an adjustable threshold signal to establish a reference voltage for each item passing said station, means storing said reference voltage to maintain the value thereof substantially constant during passage of each item through said station, means comparing the output signal of each of said sensors with said reference voltage to produce a flaw signal output from any one of said sensors, means comparing the largest output signal of any of said sensors to a predetermined adjustable voltage to produce a presence signal denoting the presence of an item at said station, and output means responsive to the concurrence of a flaw signal and a presence signal for producing an output signal indicating a flaw in an item passing through said station.

2. The system of claim 1 further defined by means comparing said reference voltage to a predetermined adjustable voltage to produce an enable signal when said reference voltage exceeds said predetermined voltage and means receiving said flaw signal and said enable signal for passing said flaw signal to said output means only upon concurrence of said flaw signal and enable signal.

3. The system of claim 1 further defined by means generating a reset signal upon termination of said presence signal and means controlled by said reset signal for discharging said means storing said reference signal and maintaining said means discharged until said presence signal is again produced.

4. The system of claim 1 further defined by the items to be inspected having a central area subject to flaws to be detected and said system further including means responsive to the initiation of said presence signal for establishing an inhibiting time delay of a duration related to the velocity of items passing said line of sensors for preventing generation of said output signal during said time delay to preclude flaw indication prior to passage of said central area over said line of sensors.

5. The system of claim 4 further defined by means comparing said reference signal to a predetermined adjustable voltage to produce an enable signal only when said reference signal exceeds said predetermined voltage, means connected to receive said flaw signals and generating a predetermined time delay therefrom and a compare signal at the end of said time delay, and means passing a flaw signal to said output means only during concurrence of said presence and compare signals for ensuring generation of an output signal only when an item is disposed between said light source and line of sensors.

6. An inspection system for detecting flaws in items normally subject to physical variation between successive items and comprising a light source, a line of light sensors disposed to receive light from said source, means passing items to be inspected in single file between said source and said line of sensors transversely of said line of sensors for intercepting light from said source, compensation circuitry for physical variation between successive items connected to said sensors for producing a reference voltage for each of said items from the average of the output of predetermined sensors for each of said items and comparing each sensor output for an item to said reference voltage for that item, then producing a flaw signal from any one of said comparisons wherein a predetermined difference exists, said circuitry further producing logic signals indicating presence of an item between said light source and said sensors from combinations of the outputs of said predetermined sensors; and logic circuitry connected to receive said flaw signals and said logic signals and producing an output signal upon the occurrence of predetermined logic combinations of signals applied to said logic circuitry as an indication of a flaw in an item passing through said station.

7. A method of inspecting items for flaws comprising the steps of passing successive items between a light source and a transverse line of light sensors, generating a sensor signal reference level from the signals from predetermined sensors of said line of sensors, comparing each sensor signal with said signal reference level to produce flaw signals from any sensor signal exceeding said signal reference level, generating a presence signal indicating the presence of an item between said light source and said sensors by comparing the signal of at least one predetermined sensor with a predetermined voltage, generating an enable signal from a comparison of said signal reference level with a second predetermined voltage, and producing an output signal upon concurrence of a flaw signal with said presence signal and enable signal as an indication of a flaw in an inspected item.

* * * * *